(12) United States Patent
de Lange et al.

(10) Patent No.: US 11,400,590 B2
(45) Date of Patent: Aug. 2, 2022

(54) OPTIMAL CONTROL OF COUPLED ADMITTANCE CONTROLLERS

(71) Applicant: Moog BV, Nieuw-Vennep (NL)

(72) Inventors: Peter de Lange, Nieuw-Vennep (NL); Richard Dijk, Nieuw-Vennep (NL); Jeffery T. Williams, East Aurora, NY (US)

(73) Assignee: Moog BV, Nieuw-Vennep (NL)

( * ) Notice: Subject to any disclaimer, the term of this patent is extended or adjusted under 35 U.S.C. 154(b) by 239 days.

(21) Appl. No.: 16/611,445

(22) PCT Filed: May 10, 2018

(86) PCT No.: PCT/EP2018/062182
§ 371 (c)(1),
(2) Date: Nov. 6, 2019

(87) PCT Pub. No.: WO2018/206750
PCT Pub. Date: Nov. 15, 2018

(65) Prior Publication Data
US 2021/0138639 A1 May 13, 2021

(30) Foreign Application Priority Data
May 10, 2017 (GB) .................................. 1707473

(51) Int. Cl.
*B25J 9/16* (2006.01)
(52) U.S. Cl.
CPC ............. *B25J 9/163* (2013.01); *B25J 9/1607* (2013.01); *B25J 9/1633* (2013.01); *G05B 2219/39339* (2013.01)
(58) Field of Classification Search
CPC .................................. B25J 9/163; B25J 9/1607
See application file for complete search history.

(56) References Cited

U.S. PATENT DOCUMENTS

| 4,398,889 A | 8/1983 | Lam et al. |
| 4,510,574 A | 4/1985 | Guittet et al. |
| (Continued) | | |

FOREIGN PATENT DOCUMENTS

| CN | 104808512 A | 5/2017 |
| EP | 0440202 A2 | 5/1998 |
| (Continued) | | |

OTHER PUBLICATIONS

International Search Report and Written Opinion of the International Searching Authority (10 pages) for International Application No. PCT/EP2018/062182, completed Sep. 27, 2018.

(Continued)

*Primary Examiner* — Kira Nguyen
(74) *Attorney, Agent, or Firm* — Harter Secrest & Emery LLP

(57) ABSTRACT

A coupling device (16, 116, 216, 316) configured optimally to communicate between a first and a second admittance controller and actuator assembly, the first and the second admittance control and actuator assembly respectively having a first and a second admittance controller (12a, 12b) configured to drive a respective first and a second actuator and each of the first and the second actuator being respectively connected to a first body having a first mass and a second body having a second mass, wherein the coupling device (16, 116, 216, 316) comprises: an input port having a first input for receiving a first input force signal (f1) from the first admittance controller and actuator assembly (12a) and a second input for receiving a second input force signal (f2) from the second admittance controller and actuator assembly (12b), and a processor adapted to derive a first output force signal for output to the first admittance controller and actuator assembly based on a Lagrange multiplier (Continued)

dependent on a comparison of the first input force signal and the second input force signal.

21 Claims, 11 Drawing Sheets

(56) References Cited

U.S. PATENT DOCUMENTS

| | | | |
|---|---|---|---|
| 6,028,409 | A | 2/2000 | Wierda |
| 6,898,484 | B2 | 5/2005 | Lemelson et al. |
| 7,688,016 | B2 * | 3/2010 | Aghili .................... B25J 9/1605 318/632 |
| 8,716,973 | B1 * | 5/2014 | Lammertse ............ B25J 9/1694 318/671 |
| 10,311,180 | B2 | 6/2019 | Belyi et al. |
| 10,675,756 | B2 * | 6/2020 | Haddadin .............. B25J 9/1633 |
| 2005/0189987 | A1 * | 9/2005 | Ohannaidh .......... H03H 11/126 327/556 |
| 2006/0142657 | A1 * | 6/2006 | Quaid ................. A61F 2/30942 600/424 |
| 2007/0073442 | A1 * | 3/2007 | Aghili .................... B25J 9/1605 700/245 |
| 2014/0222207 | A1 * | 8/2014 | Bowling .................. B25J 13/00 700/261 |
| 2016/0089211 | A1 | 3/2016 | Bowling |
| 2017/0119347 | A1 * | 5/2017 | Flores, II ............... A61B 8/488 |
| 2018/0158152 | A1 * | 6/2018 | Jereminov ................ H02J 3/16 |

FOREIGN PATENT DOCUMENTS

| | | |
|---|---|---|
| EP | 2975544 A1 | 1/2016 |
| EP | 3138665 A1 | 6/2021 |
| KR | 20150129225 A | 11/2015 |
| WO | 1991011298 A1 | 8/1991 |
| WO | WO 2008/090683 A1 | 7/2008 |
| WO | 2014028557 A1 | 2/2014 |

OTHER PUBLICATIONS

Lagrange, J. L., Mécanique Analytique vol. 1 (1811), Boston Studies in the Philosophy of Science, vol. 191 (1997).

Van Der Linde, R.Q. and Schwab, A. L., Multibody Dynamics B, 1997/1998, Delft University of Technology.

Hogan, Neville, Impedance Control: An Approach to Manipulation: Part 1—Theory, Journal of Dynamic Systems, Measurement, and Control, vol. 107/1, Mar. 1985.

Japanese Office Action (2 pages) dated May 10, 2022.

* cited by examiner $$\begin{bmatrix} U1 \\ U2 \end{bmatrix} = \begin{bmatrix} [U] \\ u1\ u2\ u3\ u4\ u5\ u6 \\ u1\ u2\ u3\ u4\ u5\ u6 \end{bmatrix} \begin{bmatrix} F1*\lambda 1 \\ F2\lambda 2 \\ K1*\theta 1 \\ K2*\theta 2 \\ C1*\omega 1 \\ C2*\omega 2 \end{bmatrix} = \begin{bmatrix} \lambda 1 & 0 \\ 0 & \lambda 2 \\ K1 & 0 \\ 0 & K2 \\ C1 & 0 \\ 0 & C2 \end{bmatrix} \begin{bmatrix} F1 \\ F2 \\ \theta 1 \\ \theta 2 \\ \omega 1 \\ \omega 2 \end{bmatrix}$$

Where (2DOF):
$\lambda 1 = 1 + M2/(M1+M2)$
$\lambda 2 = 1 + M2/(M1+M2)$
$[U] = \begin{matrix} 1\ -1\ 1\ -1\ 1\ -1 \\ 1\ -1\ 1\ -1\ 1\ -1 \end{matrix}$
$\lambda 1max, \lambda 2Max$ = Saturation level

(38)
$$\begin{bmatrix} U1^I \\ U2^I \end{bmatrix} = \begin{bmatrix} [CF] \\ \text{If } U1 > \lambda 1_{max}) \text{ then} & 0 \\ (\text{Sign}(U1)*\lambda 1_{max} \\ \text{else } U1 \\ 0 & \text{If } U1 > \lambda 2_{max} \text{ then} \\ & (\text{Sign}(U2)*\lambda 2_{max} \\ & \text{else } U2 \end{bmatrix} \begin{bmatrix} U1 \\ U2 \end{bmatrix}$$

*FIG. 10*

OPTIMAL CONTROL OF COUPLED ADMITTANCE CONTROLLERS

FIELD OF THE INVENTION

The invention relates to controlling admittance controlled actuators. In particular it relates to coupling of multiple, for example two or more, admittance controlled actuators by means of Lagrange multipliers, or modified Lagrange multiplier, for haptic applications, and also to a coupling controller, implementing the (modified) Lagrange multipliers, for controlling one, two or more admittance controlled actuators

BACKGROUND OF THE INVENTION

It is known from U.S. Pat. No. 6,028,409, incorporated herein by reference, to couple two remote control systems to enable use of one of the systems accurately to drive the other system, by use of a model follower controller having a simulated mass representative of the sum of the masses manipulated by both the remote control systems. By simulating the sum of the masses, the model follower controller enable the manipulation force on one controller not only to move the manipulable mass of the one controller but also to achieve equivalent movement at the other controller.

Admittance control was first patented in U.S. Pat. No. 4,398,889 which describes the use of an admittance controller for flight simulation devices. In this type of control, force acts as the primary control input, which results in a position output after dividing by mass and integrating twice with respect to time. FIG. 1 illustrates the admittance control loop described in U.S. Pat. No. 4,398,889. This particular type of admittance control assumes a virtual mass to be exerted by the difference between the measured force and demanded force resulting in commanded acceleration, which is integrated with respect to time to obtain a commanded velocity, which again is integrated resulting in commanded position. The commanded acceleration, velocity and acceleration are used to calculate the actuator setpoint velocity which drives the actuator position.

Limitations of current technology include that they are only valid for the specific case when initial conditions of x1(t) and x2(t) are equal, only provide specific solution for the constraint x1(t)=x2(t), and or do not allow for specialized coupling behavior such as simulating break out behavior where coupling force between both controls is capped. The invention seeks to avoid or at least mitigate these and other problems of the prior art.

SUMMARY OF THE INVENTION

One aspect of the invention provides a coupling device (16, 116, 216, 316) configured optimally to communicate between a first and a second admittance controller and actuator assembly, the first and the second admittance control and actuator assembly respectively having a first and a second admittance controller (12a, 12b) configured to drive a respective first and a second actuator and each of the first and the second actuator being respectively connected to a first body having a first mass and a second body having a second mass, wherein the coupling device (16,116, 216, 316) comprises:

an input port having a first input for receiving a first input force signal (f1) from the first admittance controller and actuator assembly (12a) and a second input for receiving a second input force signal (f2) from the second admittance controller and actuator assembly (12b), and a processor adapted to derive a first output force signal for output to the first admittance controller and actuator assembly based on a Lagrange multiplier dependent on a comparison of the first input force signal and the second input force signal and at least one characteristic of at least one of the first and the second admittance control and actuator assembly.

Other aspects and features of the invention will be apparent from the specification as a whole as well as those defined in the appended claims.

Beneficially, control according to the invention involves actuators capable of measuring both force and position where force is the primary control input of an admittance based controller. This patent application describes the use of (modified) Lagrange multipliers to calculate a virtual force which is then added to demanded force within the admittance control loop of each actuator, resulting in an optimal coupling. Use of modified Lagrange multipliers allows for simulation of coupled actuators, solve initial condition problems, fading of coupling forces, and simulating break out conditions where actuators are coupled up till a certain force level. Possible applications include robotics, haptic simulation devices and telemanipulation devices, and simulation devices such as control loading systems used for flight simulation.

Additionally, the invention includes control via a centralized controller coupled to one or more admittance controllers, a local configuration of directly coupled (communicating) admittance controllers, and a distributed configuration for example, or a mixture of the above. One can mix and match between these configuration options for each (set of) admittance controller(s). Consider for example N systems connected over the internet, where each system has K admittance controllers, which are coupled using N coupling controllers (one for each system in a 'local' configuration). One can also have the distributed system use K coupling controllers in a 'distributed' configuration, but use the 'local' configuration for all others. Beneficially, the architecture is extremely flexible; the force inputs from all admittance controllers at each coupling controller are required, and then each coupling controller output is coupled to any given set of admittance controllers. Additionally, the system can be configured such that controllers have a peer-to-peer relationship or a master-slave relationship, wherein many of the devices can assume a master role.

SUMMARY OF THE FIGURES

Detailed embodiments of the invention will now be described, by way of example only, with reference to the accompanying figures, in which:

FIG. 10 is an example of the Lagrange multiplier according to the invention.

DETAILED DESCRIPTION

The coupling solution proposed by U.S. Pat. No. 6,028,409 assumes the initial conditions with respect to time of x1 and x2 to be equal (or at least that these conditions are met over time). This assumption is not always valid, as the positions x1 and x2 may be different before the coupling is enabled or due to integration errors build up during control operation.

In this patent application, a more robust coupling mechanism is proposed which is based on the Lagrange multiplier method from multi-body dynamics. This is then further extended by enhancing the Lagrange multipliers with additional terms, which allows for simulation of specialized coupling behavior where the coupling force might be force dependent, and/or further dependent on position and/or velocity. The following modified Lagrange multiplier has been determined to enable improvement:

$$\hat{\lambda}_k(\lambda_q, x_i, \dot{x}_i) \qquad \text{Eq. 1}$$

where the modified Lagrange multiplier $\hat{\lambda}_k$ is a function of the Lagrange multipliers $\lambda_q$ and positions $x_i$ and velocities $\dot{x}_i$ Some examples are now presented for two degree of freedom systems (n=2), with masses m1, m2, positions x1, x2 and forces f1, f2. The Lagrange multiplier to couple this system such that x1(t)=x2(t) for direct coupling, and g1x1(t)=g2x2(t) for geared coupling.

In order to better deal with the initial condition problem a modification is given for addressing the case where the initial conditions of x1, x2 are different at a particular point in time (to), e.g.

$$x_1(t_0) \neq x_2(t_0) \text{ and/or } \dot{x}_1(t_0) \neq \dot{x}_2(t_0) \qquad \text{Eq. 2}$$

The modification involves the addition of a virtual spring and damper which act as a natural (physical) controller between the two degrees of freedom x1 and x2. A physical representation of this mechanism can be expressed as:

$$\hat{\lambda} = \lambda + k(x_1 - x_2) + c(\dot{x}_1 - \dot{x}_2) \qquad \text{Eq. 3}$$

With stiffness k and damping coefficient c and where $\hat{\lambda}$ yields the modified coupling force. By tuning of the coefficients c and k, the modification ensures that the differences in initial conditions between x1 and x2 will be minimized to zero over time. In case of matching initial conditions, the added terms are zero, and the Lagrange multiplier will simulate an infinite stiff coupling.

Figure 1:
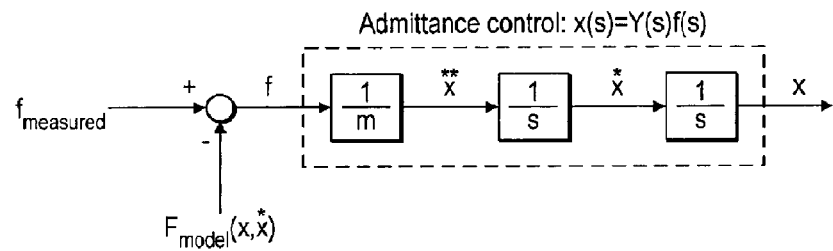
FIG. 1 is a second order admittance controller Y(s) with force input F, virtual mass m, position x and where s denotes the Laplace operator. Typically the input force f consists of both measured force $f_{measured}$ and virtual model force $f_{model}$.
Figure 2:
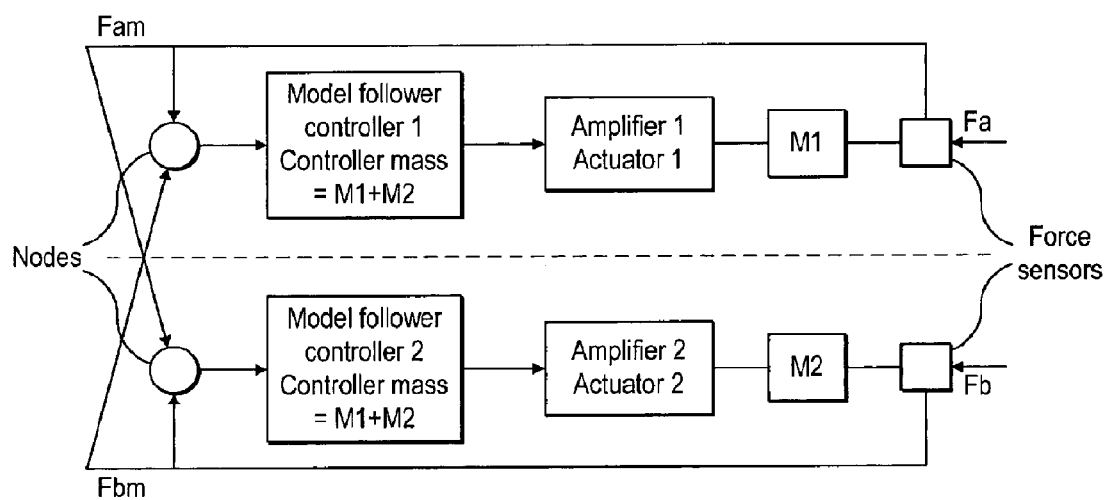
FIG. 2 is a model of a pair of coupled admittance controllers according to the prior art.
Figure 3:
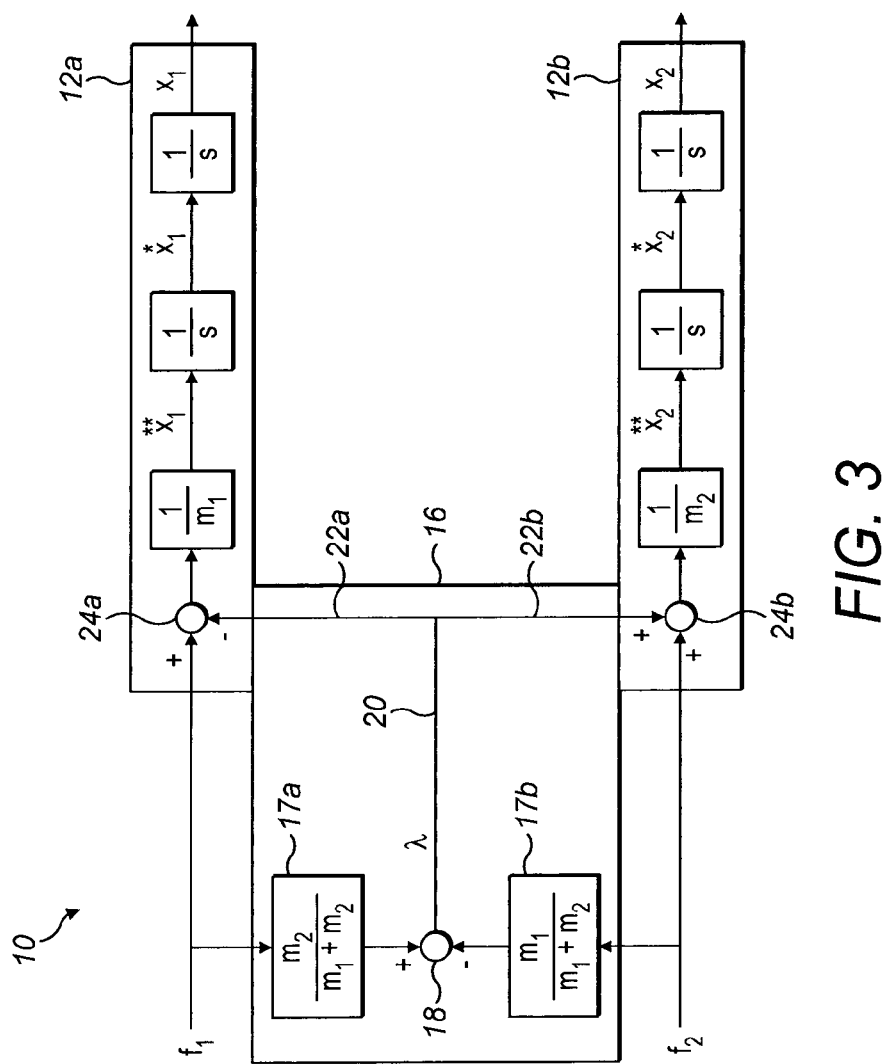
FIG. 3 is a coupled control loop by means of a Lagrange multiplier
Figure 4:
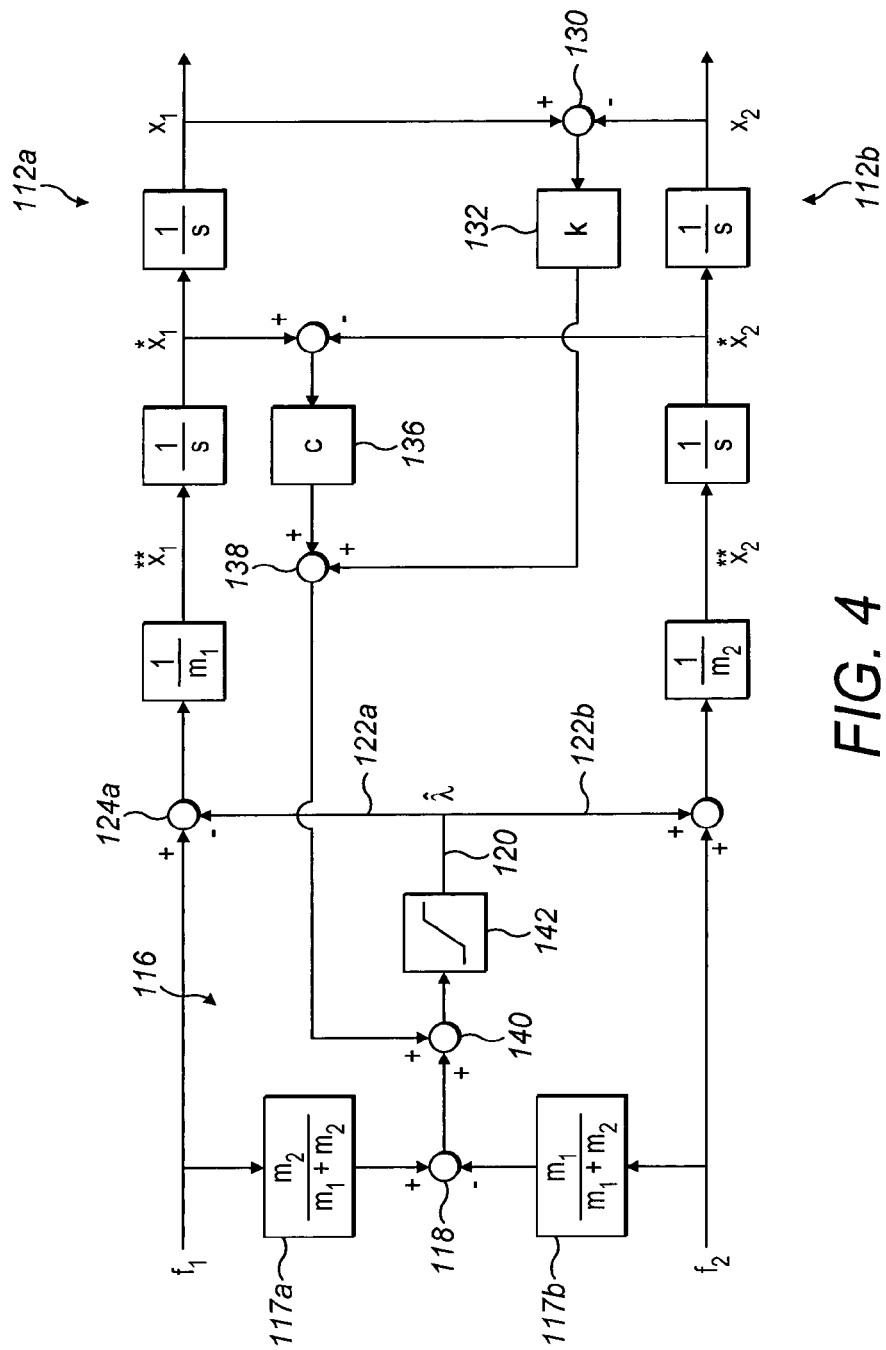
FIG. 4 is a coupled control loop through modified Lagrange multiplier, comprising virtual spring and damping components, according to the invention.

Referring to FIGS. 3 and 4, a schematic diagram of the actuator control mechanism just described is presented. Referring first to FIG. 3, there is shown a schematic block diagram of coupled control assembly 10 comprising a first admittance controller 12a and second admittance controller 12b have force inputs 14a and 14b respectively. Control assembly 10 further comprises a coupling device 16, which could be embodied in a hardwired electronic form or computer controlled system (for example comprising microprocessors and/or other programmable control devices).

The initial input forces f1 and f2 (at least one of which might be in part if not totally derived from human operator for example (and at least one of which might be in part if not totally derived from a signal from the coupling device via the respective actuator)) are fed to the coupling controller 16 via an input port into a computational array comprising a number of features such as first block functions 17a and 17b, and node 18. The first block function determines a force modified by a lumped mass equation, for example (f1m2)/(m1+m2), the output from which is fed to node 18. The resultant force is derived at node 18 from the difference in the input forces f1 and f2 acting on lumped masses m2/(m1+m2) and m1/(m1+m2) respectively. The resultant Lagrange multiplier (lambda) is fed out at output 20 from the coupling device 16, and on to inputs 22a and 22b of the respective admittance controllers 12a and 12b. Thereafter, the initial input f1 is modified by the Lagrange multiplier at node 24a, and the resultant force from node 24a is used to determine the acceleration (double dot x1) by dividing by mass m1 (upon which the actuator controlled by admittance controller 12a acts), the velocity (dotx1) and the position x1 of the mass m1. This is achieved by known calculation and integration techniques indicated in FIG. 3 based on Newtonian mechanics. Similarly, these three variables of acceleration, speed and position are determined for the mass m2 which admittance controller 12b acts on via a respective actuator (not shown). The output from each of the admittance controllers 12a and 12b is fed to an actuator to drive the respective masses m1 and m2.

Referring now to FIG. 4, the system described above comprising a virtual spring and damper are shown in FIG. 4. In this block diagram, components having the same or similar function to those shown in relation to FIG. 3 are given the same two digit reference number prefixed to the number 1. Accordingly, the coupled admittance controller assembly 110 comprises a first admittance controller 112a and second admittance controller 112b. The coupling controller 116 comprises node 118 for comparison of the resultant forces derived as in embodiment shown in FIG. 3, such that input force f1 is modified by multiplying by the ratio of m2/(m1+m2) for example.

The resultant force from comparison node 118 is fed into a further node 140. The other input to node 140 is derived as shown in FIG. 4. Firstly, a difference in position of x1 and x2 is determined by comparison node 130 and this difference is modified by a friction constant k as indicated at friction parameter block 132. A comparison of the velocities dotx1−dotx2 is made at comparison node 134 and this is modified by the damping constant C as shown at damping parameter block 136. The outputs from damping block 136 and friction block 132 are then added at the comparison node 138. The resultant output from node 138 is fed to node 140 for comparison with the force output from node 118, and the Lagrange multiplier is determined at computation block 142.

The resultant Lagrange multiplier, hat lambda, is output from the coupling controller 116 to inputs 122a and 122b to respective admittance controllers 112a and 112b. Again, a modification of the input force f1 and hat lambda is made at node 124a and a modification of input force f2 with hat lambda at mode 124b, whereby the modification involves summing or subtracting the forces as appropriate dependent of the configuration of the assembly 110. Here f1−hatlambda results in the appropriate output force from node 124a. The subsequent determination of acceleration, velocity and position in the admittance controllers 112a and 112b has the beneficial effect of bringing the control of masses m1 and m2 into agreement.

Where there is gearing then g1x1=g2x2 and hence the stiffness factor becomes k(g1x1−g2x2) and similar for the damping coefficient c(g1x1−g2x2). Indeed, it will be apparent that to unify initial conditions one can add a virtual damper and spring, that this in then incorporated in the modified Lagrange multiplier part, and that the formula one uses needs to be compatible with (restorative with respect to) the constraints. Hence, the determination of the formula above is determined based on the relevant constraints such as gearing.

Limiting the coupling force: By limiting the coupling force, special effects such as break out behavior between two haptic controls can be simulated. This is useful for flight simulation applications, where a torque breakout tube allows the pilot and copilot controls to be decoupled in case of a high force delta.

The coupling force can be capped by limiting the maximum absolute value of the Lagrange multiplier according to:

$$\hat{\lambda} = \begin{cases} \lambda_{max} \cdot \text{sign}(\lambda), & \text{if } |\lambda| > \lambda_{max} \\ \lambda, & \text{otherwise} \end{cases} \quad \text{Eq. 4}$$

with a maximum coupling force level lambda max and where had, indicates the modified Lagrange multiplier. This capped or modified Lagrange multiplier can be determined at the Lagrange computation block 142 shown in FIG. 4 for example. Similarly, an example is presented which shows in equation 5 how modified Lagrange multipliers can be used to simulate a friction coupling having a friction coefficient c.

$$\hat{\lambda} = \begin{cases} \lambda_{max} \cdot \text{sign}(\lambda + c(\dot{x}_1 - \dot{x}_2)), & \text{if } |\lambda + c(\dot{x}_1 - \dot{x}_2)| > \lambda_{max} \\ \lambda + c(\dot{x}_1 - \dot{x}_2), & \text{otherwise} \end{cases} \quad \text{Eq. 5}$$

The method of Lagrange multipliers according to the invention can further easily apply to deal with more complex constraints such as a geared coupling. For this case the constraint equations might be:

$$D(x_i) = g_1 x_1 - g_2 x_2 = 0. \quad \text{Eq. 6}$$

where g1 and g2 represent gearing constants. Again by making use of the principle of virtual work and Lagrange multipliers yields:

$$\lambda = \frac{f_1 g_1 m_2 - f_2 g_2 m_1}{g_1^2 m_2 + g_2^2 m_1} \quad \text{Eq. 7}$$

Figure 5:
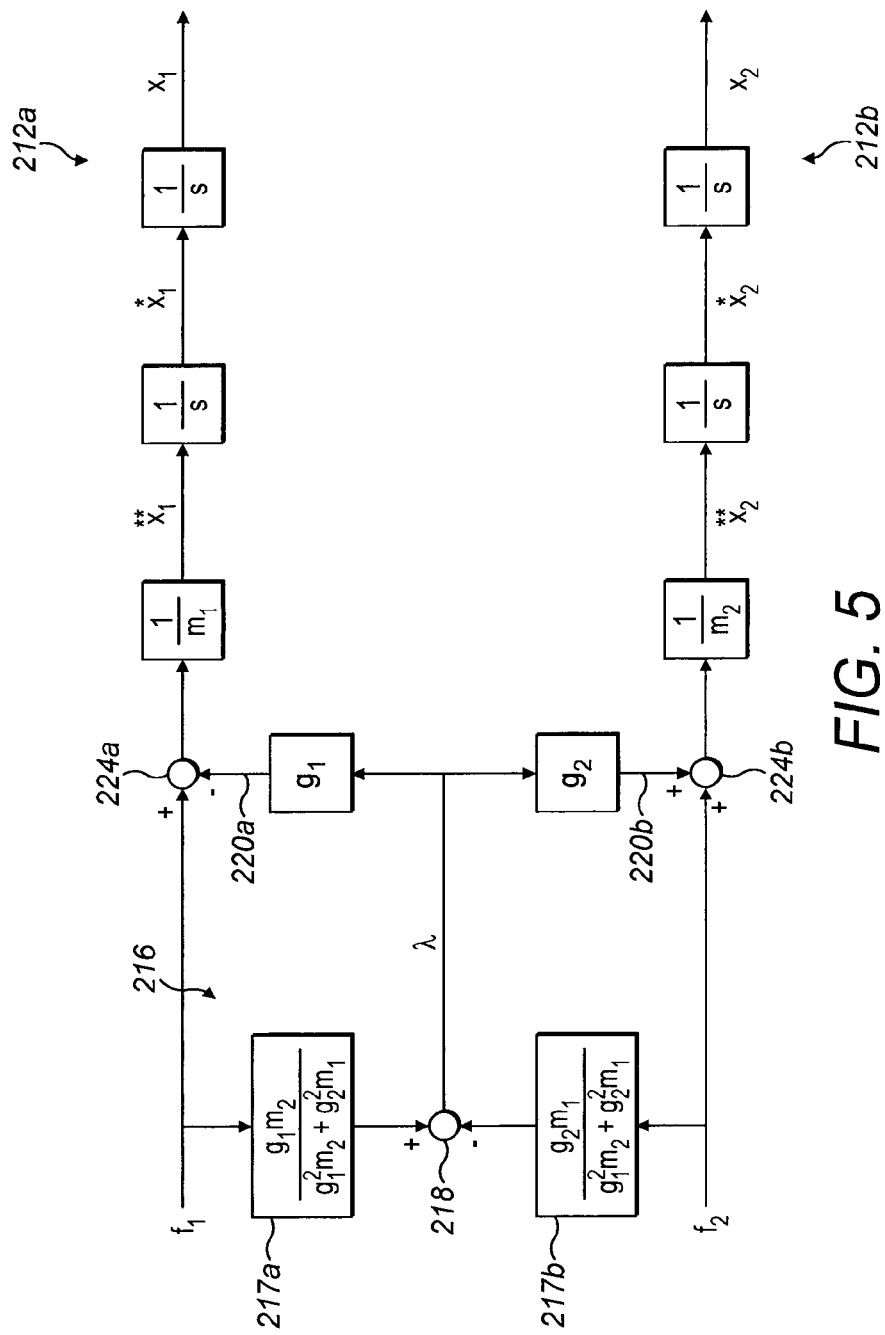
FIG. 5 is a geared coupling of control loop by means of Lagrange multiplier.

The corresponding geared and coupled control loop is shown in FIG. 5 where lambda is shown as the resultant multiplier from node 218.

Referring to FIG. 5, there is shown a third embodiment of coupled admittance controller assembly 210 similar to the earlier embodiments wherein like components are given the same two digit reference number prefixed with the number 2. Accordingly, coupled admittance controller arrangement 210 comprises a first admittance controller 212a and a second admittance controller 212b. This embodiment is similar to that shown in FIG. 3 except that the Lagrange multiplier lambda is recalculated based on the difference in gearing of the actuators controlled by the respective admittance controllers 212a and 212b. Accordingly, a gearing multiplier block g1 is used to recalculate lambda as input at mode 224a of first admittance controller 212a and similarly gearing multiplier block g2 forming part of the coupling controller 216 is used to determine lambda as input at comparison node 224b forming part of the second admittance controller 212b.

Figure 6:
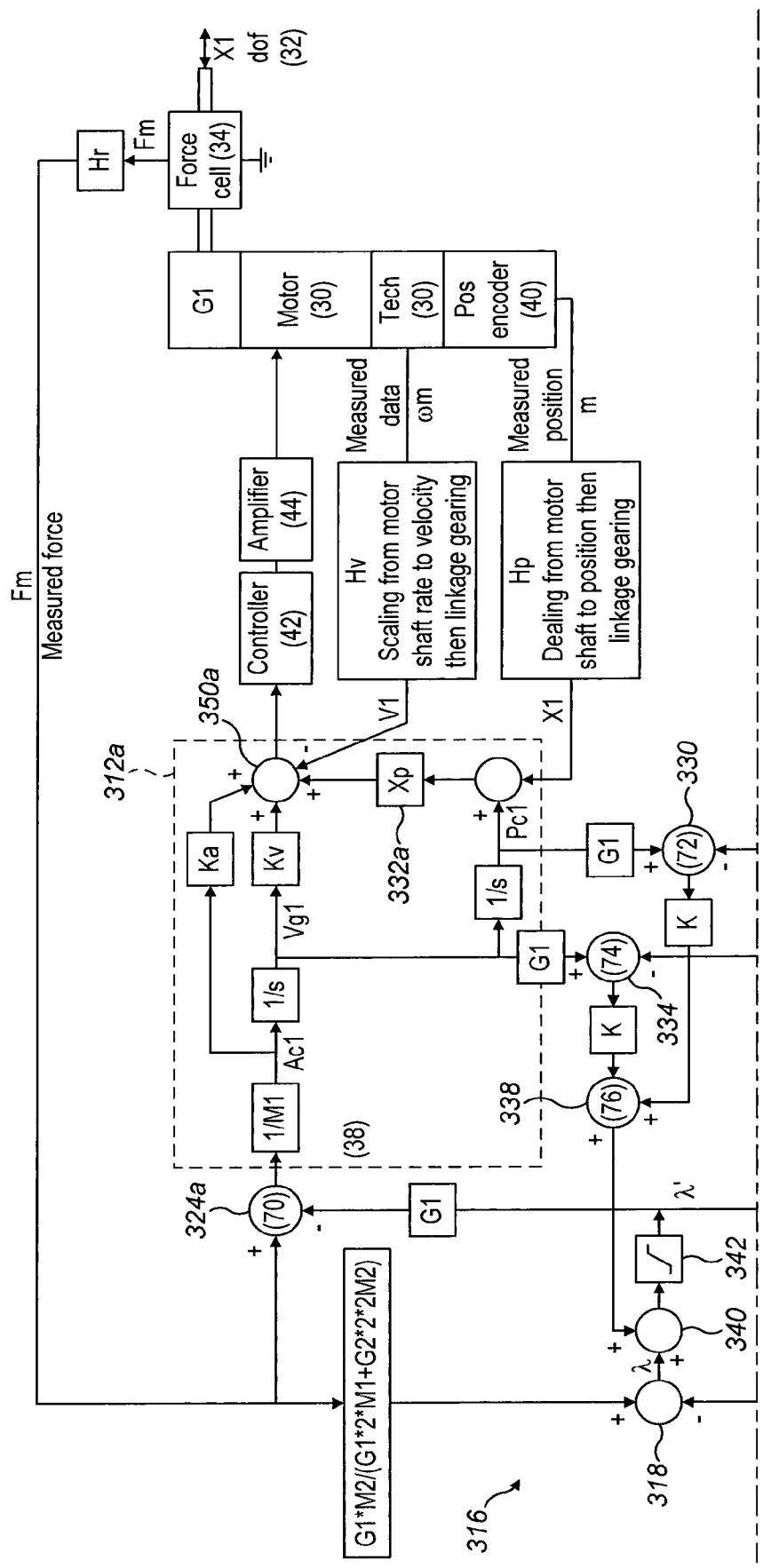
FIG. 6 is an admittance control architecture comprising geared coupling.
Figure 6:
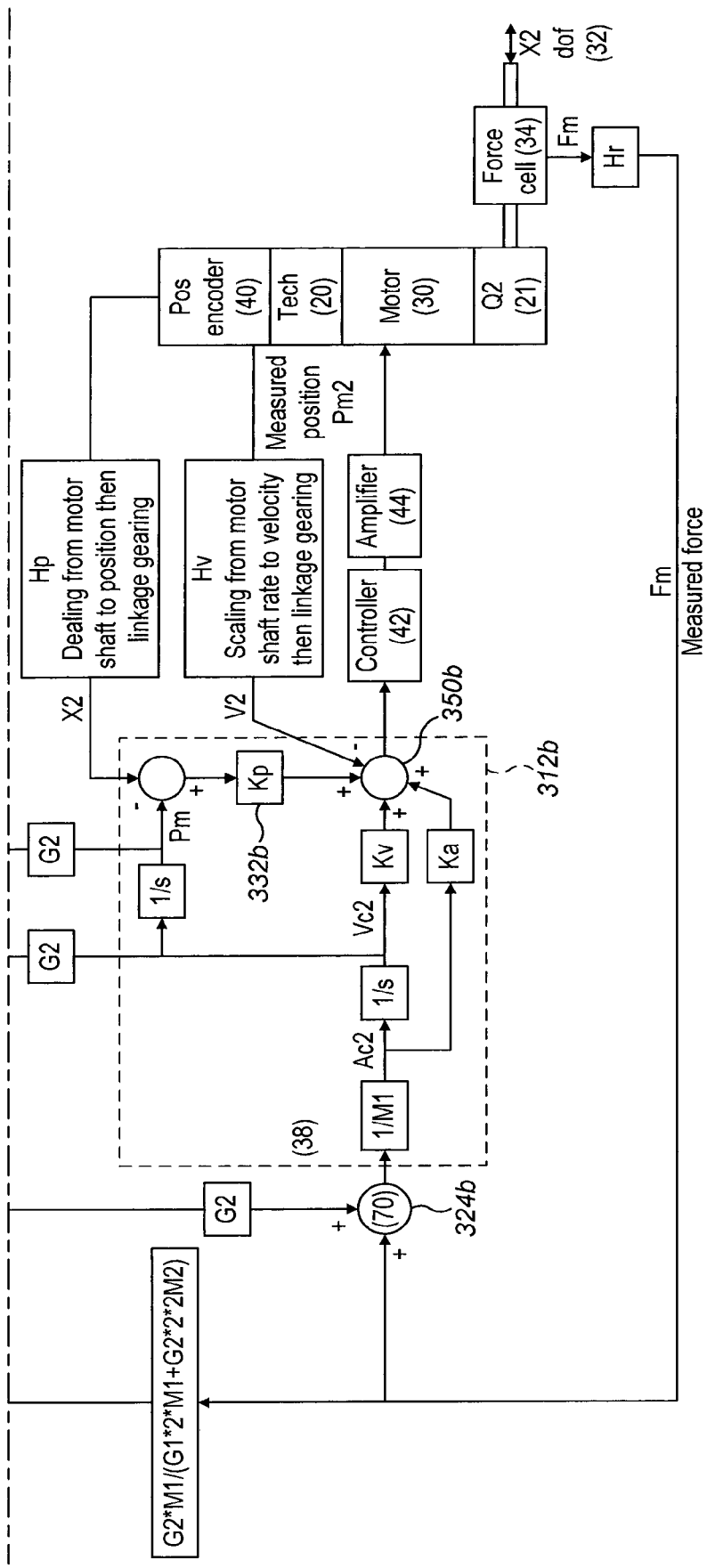

Referring to FIG. 6 there is shown an admittance control architecture for the example of geared coupling, with two single degrees of freedom systems. FIG. 6 is the architectural implementation for the embodiment of geared coupling containing mechanical and electrical elements, and includes the virtual damping/stiffness and gearing. There is shown a coupled admittance controller assembly 310 according to the invention wherein components having the same or similar functionality to those in earlier embodiments are given the same 2 digit reference number prefixed by the digit 3. So here, coupling device 316 comprises a first node 318 which determines the first stage of the Lagrange multiplier based on equation 7 above as shown in 6 and as ostensibly shown also in FIG. 5 for that geared system.

Here, however, there is shown a more complex system comprising both the dampening as well as the friction spring and gearing components. Additionally, the output from the first and second admittance controllers 312a and 312b are shown as linking to a controller through to an amplifier onto a motor which drives a mass (not shown but again mass ml in the case of the first admittance controller 312a for example). The motor operates in a single degree of freedom to drive an actuator rod for example. A force cell is provided to provide a measured force feedback loop through to node 318. Additionally, the motor comprises both a measured velocity sensor and a measured position sensor and these measured velocities and measured positions (x1, v1 and x2, v2) are fed back to the admittance controllers 312a and 312b respectively as shown in FIG. 6.

Accordingly, the coupling device 316 again receives input regarding the velocity and position from the respective admittance controllers 312a and 312b as shown in relation to the embodiment of FIG. 4 for example. Such that the comparison of the positions and velocities is able to be fed to comparison nodes 330, 334 and 338 to comparison node 340 whereby the resultant Lagrange multiplier is further calculated at the computation block 342 to determine the modified Lagrange multiplier lambda prime which is fed via gearing multiplication blocks g1 and g2 respectively to the input nodes 324a and 324b of the admittance controller 312a and 312b respectively. Notably however, the admittance controller 312a and 312b further comprise comparison nodes 350a and 350b respectively. The input to these nodes 350a and 350b are the measured velocity V1 and V2 respectively, the comparison of the measured position X1 X2 with the input out position determining from the second integrator 1/S of both of the admittance controllers 312a and 312b respectively x the spring constant calculation block 33 to a and b respectively. Further, the velocity multiplied by the spring constant block internally calculated by the admittance controllers 312a and 312b is input to comparison node 350a and 350b respectively and finally, the determined acceleration again after multiplication by the spring constant is input as a fourth input to the nodes 350a and 350b. The resultant course is fed to the controller and onto the amplifier thereby to cause the motor to drive the relevant actuation rod.

Rearranging the embodiment shown in FIG. 6 on a per channel basis, each channel may be described as a single admittance controller and a single actuator. The invention allows for the combination of multiple single channels in combination. For example certain haptic controllers would require at least 3 channels dedicated to servicing the input device and the 6 degrees of freedom input device of another haptic controller would require 6 channels. Any number of output devices can be envisioned, such as the virtual tool or an actual physical tool as in a medical robot with n channels. The coupling between the channels is made through the Lagrange multiplier procedure, optionally enhanced with Compliance and Damping matrices. FIG. 10 shows the architecture to couple two or more systems. Beneficially, each admittance controller and actuator assembly has its own identity within the network and is therefore uniquely controllable, with each assembly being equivalent to a peer-to-peer assembly optimally controlled to enable equivalent operation.

Figure 7:
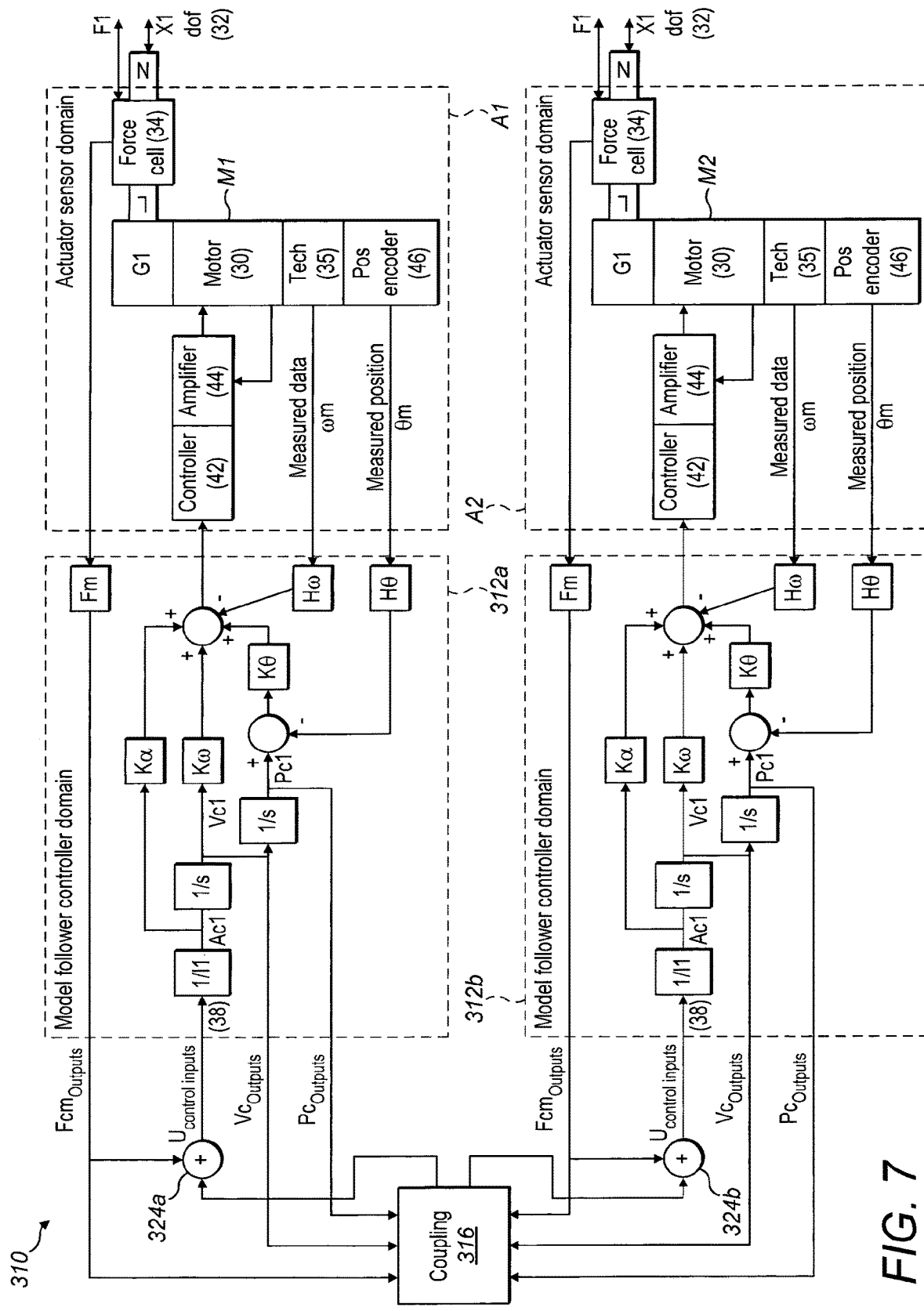
FIG. 7 is a first embodiment of the invention comprising a coupling device enabling a pair of model follower controllers to control respective actuators.

So referring to FIG. 7, there is shown a modified form of the embodiment of FIG. 6, wherein the coupling device 316 is more clearly identified. It may or may not be a separate electronic device. For example, coupling device 316 might form part of system comprising an admittance controller and or an actuator for example. Indeed, such a coupling controller might be part of two or more such systems with one acting as the primary coupling controller receiving all relevant inputs in order to determine the appropriate outputs to each assembly in a network.

Figure 8:
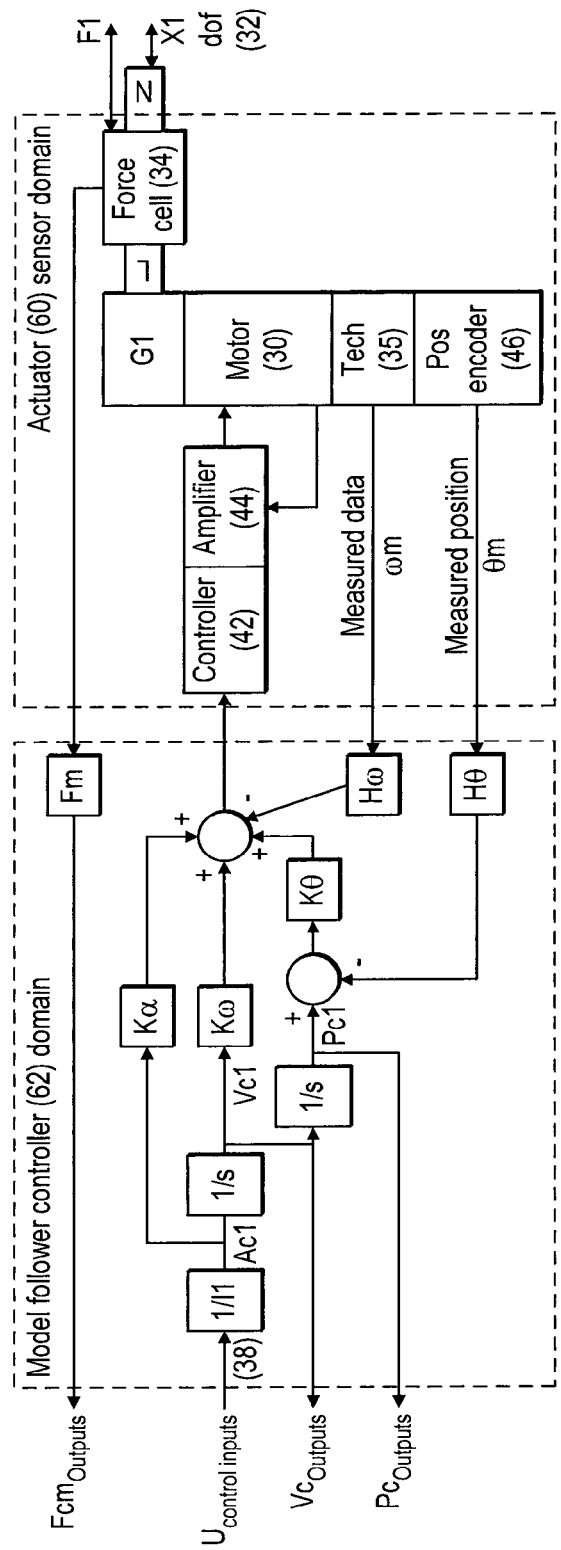
FIG. 8 is a large view of a model follower controller and actuator shown in FIG. 7.

FIG. 8 shows more clearly an individual channel from FIG. 7, as might be represented by the admittance controller 312*a* and actuator.

The coupling device 316, whilst comprising inputs and outputs fundamentally behaves as a computational device that outputs the coupling force for each system, given the positions, velocities and measured forces on all systems. When wanting to couple multiple systems, the logical steps followed are: write down the desired coupling in terms of a set of constraint equations D_k=0; and solve the constraints using the Lagrange multiplier method described, getting the λk Lagrange multiplier functions. This gives the formula to calculate the coupling forces. The coupling device 316 uses this resultant formula to calculate as its output the coupling force from the positions, velocities and measured forces.

Figure 9:
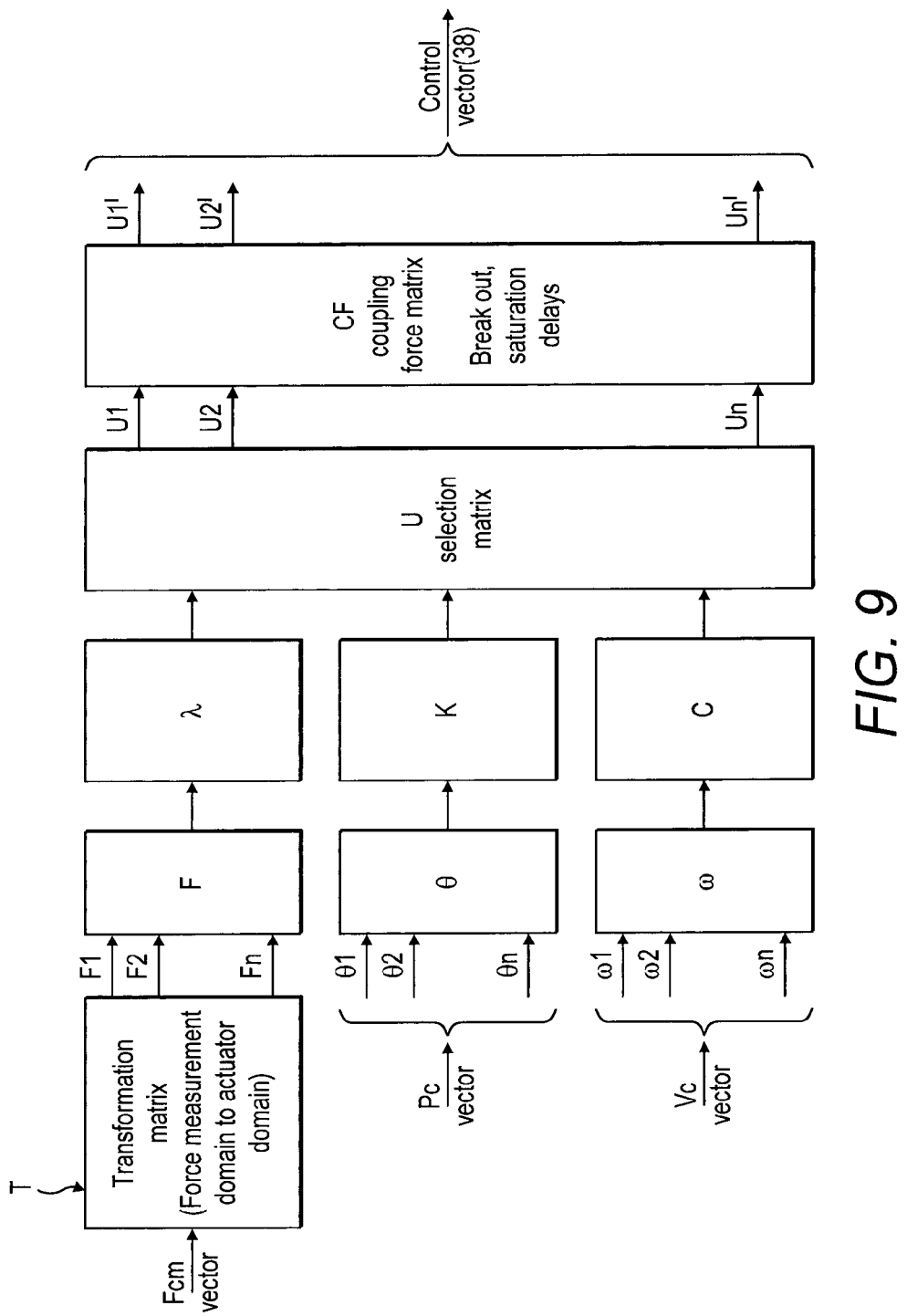
FIG. 9 is a schematic block diagram showing multiple channel control system according to the invention.

FIG. 9 shows an example specification of the coupling block for the case of linear constraints when damping and compliance functions are included and the possibility for break-out simulation is added. The specification of multichannel coupling controller for linear constraints, comprises Lagrange multiplier (λ), damping(C) and compliance(K) and coupling force(CF) variables. Here, the overall system is scaled to allow multiple (n) channels rather than the two admittance controllers 312*a* and 312*b* of FIGS. 6, 7 and 8. In FIG. 9 there is a shown a transformation function T, a force function F for input forces for each admittance controller, a Lagrange function Lambda, as a well as position and vector computation functions for example for compliance K and damping C. The outputs from the Lagrange λ, compliance K and damping C functions are processed at a selection function U, before a coupling force function CF is used to determine control outputs to the respective actuators.

The transformation function T performs the function of both the geometric transformation from and to the admittance controller 312*a* and 312*b* for example (or model follower domain) to the actuator input or load. Function T accounts for the effects of reflected mass or inertia through the gearing and linkages. FIG. 6 shows this effect in the G1/G2 blocks but assumes a linear gearing at the motor actuator stage. The transformation function T in FIG. 9 is a more general form that accounts for linear or non-linear linkages, loading and gearing at any stage. The matrix elements can be used to establish the relationships between each channel and can account for non-orthogonal cross coupling effects between channels.

The selection function U is a vector (combined outputs from the λ, C and K vector operations) multiplication. The population of the U selection matrix allows for the specifying the relationship between each channel or creating summing junctions or scaling between any channels by populating the diagonal and off diagonal matrix elements. FIG. 10 is an example of a 2 DOF system where the there is a no cross channel coupling and where the summing between the force (Fcm) is summed in the selection function U. As in FIG. 10, the summing can be outside the U selection matrix as desired. This example assumes that there is a simple saturation of the total coupling force that simulate sliding and coulomb friction and limited compliance coupling. In this example all the contributions for mass effects, compliance and damping are accounting for as in FIG. 8 through a simple saturation operator. The relationship between the U1 and U2 channels is independent, or the channels may be interrelated depending on the how the coupling force function CF is populated. By selective population of the U and CF functions, individual contributions or proportions of compliance, damping and mass effects can be applied each channel. Any type of linear or non-linear operators may be added to the force coupling function CF as well as any cross channel effects by populating the off diagonal matrix elements. This therefore provides a means of mapping each channel relative to each other by proscribing the relationship through selectively populating the elements of the coupling force function CF and mixing the channels through the selection function U.

The calculation done by the coupling force function CF to output the virtual coupling forces as deduced by the Lagrange multiplier procedure at each controller step is $$\Lambda_i = \sum_k \lambda_k(\vec{p}, \vec{v}, \vec{F}) \partial_i D_k(\vec{p}) \qquad \text{Eq. 8}$$

The Λ here corresponds to the Λ block in FIG. 9. The damping and compliance are functions of the velocities and positions that can still be chosen, in the general case; they are typically chosen to be restorative with respects to the constraints. In the case of linear constraint functions Dk, they reduce to the standard damping and compliance matrices, which are then only functions of positions and velocities respectively, such as in FIG. 9. After summing all forces related to coupling, break-out behavior can be simulated as the final step before giving as output the coupling forces between systems.

This architecture according to the invention, for instance, allows geared coupling to be sequenced with break-out simulation. It also shows that the direct coupling in the original patent is the optimal one. But it's not limited to just these; for instance, one can also envision two double-actuator systems that should be coupled such that the first system is rotated an angle α with respect to the second system. Accordingly, the only thing that needs to be done is writing down the constraints that correspond to this rotation, and the required λ, parameters come rolling out. The power of the development is then that the same architecture can be used for many different coupling behaviours and all that would need to be changed is how the λ are calculated from the commanded forces. In other words, the same manner of connecting the systems can be used for all possible interconnect functions, and all that would vary is the calculation of the λ's. The present invention improves the prior art by giving a standardised way of connecting multiple systems together.

Given a set of actuators with admittance-controllers—labelled by the index i—some of which belong to the same system and others which are remote, and the sum of measured and commanded forces f_i for each of these actuators, assumed to be connected via the architecture underlying FIGS. 3 to 6, the task is to find the coupling forces that correspond to the desired coupling. The starting point for the procedure is the desired coupling relation. These are written as a set—labelled by k—of constraint equations D_k (x)=0. The equations of motion can then be solved (analytically or numerically) to give the Lagrange multipliers λ_k, one for each constraint, where each λ_k is a function of the input forces f_i. Multi-body mechanics then tells us that the λ_k, when summed Λ_i, are the constraint forces of a physically connected system. At this point, other forces, such as restorative forces (velocity-based damping, position-based springs) can be added to give the principal (tentative) coupling force for each actuator i. The next step is that in using this architecture and procedure, the coupling force appears explicitly, so other coupling-force based simulation can be done, such as break-out simulation. The output is the final coupling force C_i for each actuator i. The calculated coupling force C_i plus the measured+commanded force f_i is then sent to the input of actuator i's admittance-controller.

Figure 11:
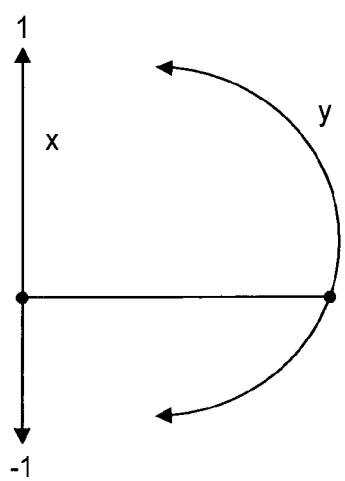
FIG. 11 is a figurative representation of a non-linear system.

Turning now to an example of a non-linear system, reference is made to FIG. 11, which is an example of the non-linear coupling of two admittance controllers, where one controller (A) moves in a straight line (−1 to +1) and the other controller (B) moves in a half-circle, with y also from −1 to +1, by keeping the projection of y onto the straight line synchronized. The constraint for this desired coupling is:

$$D = x - \sin\frac{\pi}{2} y.$$ Eq. 9

The Lagrange multiplier that follows is given by:

$$\lambda = [m_y \dot{y}^2 - m_x \dot{x}^2]^{-1}\left(m_y \dot{y}^2 F_x + m_x \dot{x}\dot{y} F_y + \left(\frac{\pi}{2}\right)^2 m_x^2 x \dot{x}\dot{y}^3\right).$$ Eq. 10

Note the possible divergence coming from the denominator, indicating the turn-over points, $$y = \pm\frac{\pi}{2},$$

where the relative directions of x and y flip instantly, which would require infinite coupling force. The (optimal) coupling forces are given by $$F_{coupling,x} = -\lambda, \; F_{coupling,y} = \frac{x}{y}\lambda.$$ Eq. 11

Explicitly visible here is that the coupling force depends non-linearly on the positions and velocities. Note that in the derivation, it was possible to replace sines and cosines of y by velocities instead, because the coupling is optimal, making the computation in the controller much quicker.

Consider now an example coupling of two admittance controllers where the equations of motion feature a non-lumped mass matrix $$M_{ij} = \begin{pmatrix} m & \mu \\ \mu & m \end{pmatrix}, \text{ with } \mu \neq 0.$$ Eq. 12

Furthermore, the coupling constraint between the two is given by an exponential:

$$D = x_1 - e^{x_2}.$$ Eq. 13

The Lagrange multiplier is then given by $$\lambda = [\mu + mx_1]^{-1}(\mu F_1 - mF_2 + (m^2 - \mu^2)A_2), \text{ with}$$

$$A_2 = [mx_1^2 + 2\mu x_1 + m]^{-1}(x_1 F_1 + F_2 - \dot{x}_1 \dot{x}_2(\mu + mx_1)),$$ Eq. 14 where $A_2$ is an expression for $\ddot{x}_2$ in terms of measured forces, positions and velocities. The resulting coupling forces are:

$$F_{coupling,x} = -\lambda - \mu A_2, \text{ and } F_{coupling,y} = x_1 \lambda - \mu x_1 A_2 - \mu \dot{x}_1 \dot{x}_2.$$ Eq. 15

Note the presence of the additional coupled mass (μ) terms from the original non-lumped system equations, which can be implemented via the coupling force.

Finally, it will be noted by those skilled in the art that among other advantages, beneficially the present invention allows of infinite stiff coupling of haptic control loops and allows for specialized simulation functionality such as breakout behavior and friction based (i.e. clutch) coupling. It provides a stable method for dealing with initial condition problems, and allows for infinite stiff break out coupling which is very applicable to the field of control loading flight simulation devices where such break out behavior requires to be simulated. The invention describes a very general and easy to implement method of constraining multiple force based admittance loops which saves time and improves quality of implementation of complex coupling constraints. The invention is not limited to the embodiments described or those shown in the figures.

The invention claimed is:

1. A coupling device configured optimally to communicate between a first and a second admittance controller and actuator assembly, the first and the second admittance control and actuator assembly respectively having a first and a second admittance controller configured to drive a respective first and a second actuator and each of the first and the second actuator being respectively connected to a first body having a first mass and a second body having a second mass, wherein the coupling device comprises:
an input port having a first input for receiving a first input force signal (f1) from the first admittance controller and actuator assembly and a second input for receiving a second input force signal (f2) from the second admittance controller and actuator assembly, and
a processor adapted to derive a first output force signal for output to the first admittance controller and actuator assembly based on a Lagrange multiplier dependent on a comparison of the first input force signal and the second input force signal and at least one characteristic of at least one of the first and the second admittance control and actuator assembly.

2. A coupling device according to claim 1 wherein the Lagrange multiplier is dependent on a holonomic constraint of at least one of the first and the second admittance control and actuator assembly.

3. A coupling device according to claim 1 wherein the at least one characteristic is the mass of at least one of the first mass and the second mass.

4. A coupling device according to claim 1 wherein the processor is adapted to derive a second output force signal for output to the second admittance control and actuator assembly.

5. A coupling device according to claim 4 wherein the first and the second output force signals are the same.

6. A coupling device according to claim 1 wherein the processor determine a force difference in the first input force and the second input force after each is multiplied by the lumped mass equivalent for the other assembly.

7. A coupling device according to claim 6 wherein the force difference is determined between the first input force multiplied by the second mass (m2) divided by the sum of the first and second masses (m1+m2), and the second input force multiplied by the first mass (m1) divided by the sum of the first and second mass (m1+m2), according to the equation delta=((f1m2)−(f2m1))/(m1+m2).

8. A coupling device according to claim 1 adapted to operate when the first and the second admittance control and actuator assemblies comprise different gearing ratios (g1, g2) to drive the respective first mass (m1) and second mass (m2), whereby the processor derives a difference in input forces from the first and the second assemblies dependent on the difference in gearing ratios of the first and the second assemblies.

9. A coupling device according to claim 8 wherein the force difference is determined based on a computation dependent on the square of the gearing ratios g1 and g2 of the first and second assemblies and given as delta= ((f1g1m2)−(f2g2m1))/(g1$^2$m2+g2$^2$ m1)).

10. A coupling device according to claim 8 wherein the first output force from the coupling device to the first assembly is further modified by the first assembly gearing ratio (g1) and the second output force from the coupling device to the second assembly is further modified by the second assembly gearing ratio (g2).

11. A coupling device according to claim 1 wherein the input port is further adapted to receive a third signal from the first admittance controller and actuator assembly and a fourth signal from the second admittance controller and actuator assembly, which third and fourth signal are representative of a variable of the first and the second admittance controller and actuator assembly, whereby the coupling device analyses the third and fourth signal to derive a first and a second output force signal for output to the first and to the second admittance controller and actuator assembly which is based on a Lagrange multiplier dependent on both the third and fourth signal.

12. A coupling device according to claim 11 wherein the variable is at least one of position, velocity and acceleration, and wherein the variable is a derived variable based on the input force and determined from Newtonian mechanics.

13. A coupling device according to claim 12 wherein the variable is a measured variable of the respective assembly.

14. A coupling device according to claim 11 wherein the processor enables comparison of a position input variable and use of a virtual spring to effect the actual positions of the masses m1 and m2 to remain consistent with one another.

15. A coupling device according to claim 11 wherein the processor enables comparison of a velocity input variable and use of a virtual damping effect to achieve the effect that the positions of the masses m1 and m2 to remain consistent with one another.

16. A coupling device according to claim 1 wherein the processor enables a maximum force setting thereby to enable "break-out" of at least one admittance controller from another.

17. A coupling device according to claim 1 wherein the input port is configured to receive inputs from 2 or more controller assemblies and to provide output force feedback to each in a plurality of configurations comprising at least one of a peer to peer configuration, a peer to many configuration, a master to slave configuration, a master to plural slave configuration, and a many to many configuration.

18. A coupling device configured to enable optimal control of three or more admittance controller and actuator assemblies, each assembly having an admittance controller configured to drive an actuator connected to a body having a mass, wherein the coupling device comprises:
an input port having an input for receiving input force signals from the admittance controller and actuator assemblies, and
a processor adapted to derive an output force signal for output to each of the admittance controller and actuator assemblies based on individual characteristics of a particular admittance controller and actuator assembly and on a comparison of the input force signals.

19. A distributed system of actuators comprising a coupling device of claim 1.

20. A distributed system according to claim 19 comprising a pair of admittance controller and actuator assemblies which are coupled together.

21. An admittance controller and actuator assembly comprising a coupling device according to claim 1.

* * * * *